United States Patent
Noguchi et al.

(10) Patent No.: US 6,399,658 B1
(45) Date of Patent: Jun. 4, 2002

(54) COMPOSITION CONTAINING ASCORBIC ACID

(75) Inventors: Hiroshi Noguchi, Kawanishi; Mutsuo Taiji, Takatsuki; Hiroshi Yamaga, Suita; Yasushi Itakura, Nara; Junji Ichihara, Takatsuki, all of (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/319,573

(22) PCT Filed: Dec. 17, 1997

(86) PCT No.: PCT/JP97/04662

§ 371 (c)(1),
(2), (4) Date: Jun. 9, 1999

(87) PCT Pub. No.: WO98/27982

PCT Pub. Date: Jul. 2, 1998

(30) Foreign Application Priority Data

Dec. 24, 1996 (JP) ............................................. 8-356302

(51) Int. Cl.[7] ........................ A61K 31/34; A61K 31/155
(52) U.S. Cl. ........................ 514/474; 514/635; 514/922; 514/936
(58) Field of Search ................................ 514/474, 635, 514/922, 936

(56) References Cited

U.S. PATENT DOCUMENTS

| | | | | |
|---|---|---|---|---|
| 3,864,496 A | * | 2/1975 | Diamond et al. | 424/326 |
| 3,874,384 A | * | 4/1975 | Deindoerfer et al. | 128/272 |
| 4,028,402 A | | 6/1977 | Fischer et al. | 260/501.14 |
| 4,089,957 A | * | 5/1978 | Jonsson | 424/248.56 |
| 5,260,275 A | * | 11/1993 | Cooper et al. | 514/12 |
| 5,324,748 A | * | 6/1994 | Horrobin | 514/560 |
| 5,656,286 A | * | 8/1997 | Miranda et al. | 424/449 |

FOREIGN PATENT DOCUMENTS

JP   7-126162 A   5/1995

OTHER PUBLICATIONS

Sernov et al., Farmakologiia i Toksikologiia, vol. 54, No. 4, pp. 24–6 (Jul./Aug. 1991) (with English Abstract).

Evans et al., Biochem. Pharmacol., vol. 32, No. 22, pp. 3459–3463 (1983).

* cited by examiner

*Primary Examiner*—Frederick Krass
*Assistant Examiner*—Donna Jagoe
(74) *Attorney, Agent, or Firm*—Birch, Stewart, Kolasch & Birch, LLP

(57) ABSTRACT

L-ascorbic acid, L-ascorbic acid derivatives and salts thereof can reduce lactic acid levels in blood, and are useful for treating lactic acidosis and the like caused by administration of amoxapine, theophylline, metformin, phenformin, buformin, nalidixic acid, hopantenic acid, azidothymidine, dideoxycytidine, high caloric transfusion, propylene glycol, ethylene glycol, xylitol, lactose, sorbitol or the like.

6 Claims, No Drawings

COMPOSITION CONTAINING ASCORBIC ACID

This application is the national phase under 35 U.S.C. § 371 of PCT International Application No. PCT/JP97/04622 which has an International filing date of Dec. 17, 1997, which designated the United States of America.

TECHNICAL FIELD

The present invention relates to a composition containing L-ascorbic acid, an L-ascorbic acid derivative or a salt thereof as an active ingredient. The composition of the present invention has the effect of reducing lactic acid levels in blood, and is useful, for example, for reducing side effect caused by a drug which has lactic acidosis as a side effect.

BACKGROUND ART

Lactic acidosis is a state in which the lactic acid level in blood is 45 mg/dL or more, and pH of arterial blood is 7.25 or less. As to clinical symptoms, though lactic acidosis usually does not result in any symptoms in the early stage, later there appear, for example, low blood pressure, unconsciousness, nausea, vomiting, stomach ache, diarrhea, muscular ache, the state of hyperventilation and circulatory disorder etc. These symptoms often occur especially severely in elderly persons and patients with cardiac or renal disease etc.

Certain kind of drugs and medical supplements are known to cause lactic acid levels to increase in blood as a side effect and to induce lactic acidosis. After lactic acidosis occurs, usage of the drugs and the medical supplements may be restricted, because of the possibility that they might worsen renal failure etc.

Biguanide compounds have excellent activity in reducing blood sugar levels. Therefore they have long been used as a medicament for treating diabetes, as have sulfonylureas (SU). Since some biguanide compounds have recently been found to have a unique pharmacological profile that they do not promote insulin secretion, do not induce fatness, and improve insulin resistance, biguanide compounds such as metformin (1,1-dimethylbiguanide hydrochloride) have been paid attention. However, biguanide compounds are known to cause hyperlactatemia (Brit.Med.J., 5794/1, 205–206(1972)) and lactic acidosis (Acta.Med.Scand., 191, 203–208 (1972)) as a side effect by inducing accumulation of lactic acid. In fact, phenformin (1-(2-phenethyl) biguanide), a biguanide, is known to cause often serious lactic acidosis as a side effect.

A dichloroacetic acid salt of a biguanide compound is reported as a safer drug (JP 51-125718 (A)). However, dichloroacetic acid has comparatively strong toxicity ($LD_{50}$/rat oral: 2820 mg/kg), so the salt is not a satisfactorily safer drug.

PROBLEM TO BE SOLVED

The problem to be solved is to provide a medicament for reducing lactic acid levels in blood, and to provide a pharmaceutical composition or a compound with a reduced side effect, which contains a drug or a medical supplement which causes lactic acid levels in blood to increase as a side effect.

SOLUTION OF THE PROBLEM

The inventors of the present invention have intensively carried out research on pharmaceutical compositions or compounds for reducing side effect caused by a drug or the like which causes lactic acid levels in blood to increase as a side effect, and found that L-ascorbic acid or the like can reduce lactic acid in blood. Thus, the present invention has been accomplished.

That is, the present invention is as follows.

[1] A medicament for reducing lactic acid levels in blood containing L-ascorbic acid, an L-ascorbic acid derivative or a salt thereof as an active ingredient.

[2] A medicament according to [1] for treating lactic acidosis.

[3] A medicament according to [1] or [2] containing L-ascorbic acid as an active ingredient.

[4] A method for reducing lactic acid levels in blood comprising administrating L-ascorbic acid, an L-ascorbic acid derivative or a salt thereof.

[5] A pharmaceutical composition containing L-ascorbic acid, an L-ascorbic acid derivative or a salt thereof, and a drug or a medical supplement which causes lactic acid levels in blood to increase as a side effect.

[6] A pharmaceutical composition according to [5] wherein the drug or the medical supplement which causes lactic acid levels in blood to increase as a side effect is amoxapine, theophylline, metformin, phenformin, buformin, nalidixic acid, hopantenic acid, azidothymidine or dideoxycytidine or a salt of any of these; or high caloric transfusion, propylene glycol, ethylene glycol, xylitol, lactose or sorbitol.

[7] A pharmaceutical composition according to [5] containing L-ascorbic acid, an L-ascorbic acid derivative or a salt thereof; and a biguanide represented by formula 1:

$$R^1\underset{\underset{R^2}{|}}{N}-\underset{NH}{\overset{NH}{||}}{C}-\underset{H}{N}-\underset{NH}{\overset{NH}{||}}{C}-NH_2$$

wherein $R^1$ is hydrogen or lower alkyl;

$R^2$ is lower alkyl, optionally substituted aryl, optionally substituted aralkyl or optionally substituted aryloxy-lower alkyl; or $R^1$ and $R^2$ are taken together with the nitrogen atom to form saturated heterocyclic ring, or a salt thereof.

[8] A pharmaceutical composition according to [5], [6] or [7] wherein L-ascorbic acid, the L-ascorbic acid derivative or the salt thereof is L-ascorbic acid.

[9] A pharmaceutical composition according to any one of [5] to [8] wherein the dose of L-ascorbic acid, the L-ascorbic acid derivative or the salt thereof is in the range between about 50 mg/day and about 10 g/day.

[10] A salt formed from L-ascorbic acid or an L-ascorbic acid derivative and a drug having basic group(s) which causes lactic acid levels in blood to increase as a side effect.

[11] A salt according to [10] wherein the drug having basic group(s) which causes lactic acid levels in blood to increase as a side effect is a biguanide represented by formula 1:

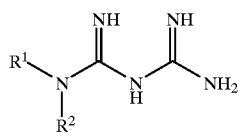

wherein $R^1$ and $R^2$ are as defined above.

[12] A salt according to [10] wherein the drug having basic group(s) which causes lactic acid levels in blood to increase as a side effect is metformin, phenformin or buformin.

[13] A salt according to [10] wherein the drug having basic group(s) which causes lactic acid levels in blood to increase as a side effect is metformin.

[14] A salt according to any one of [10] to [13] wherein L-ascorbic acid, the L-ascorbic acid or the salt thereof is L-ascorbic acid.

[15] A medicament containing a salt according to any one of [10] to [14].

[16] A medicament for treating diabetes containing a salt according to any one of [10] to [14].

[17] A method for treating diabetes comprising administrating a salt according to any one of [10] to [14].

"L-Ascorbic acid derivative" includes any L-ascorbic acid derivatives which have a pharmacological effect as Vitamin C, such as esters, stereoisomers, glycosides, aminated derivatives, ethers and the like of L-ascorbic acid ("Unknown Abilities of L-Ascorbic Acid" Kumao Ebihara, ed. by Maruzen (1992)).

"Ester of L-ascorbic acid" includes esters esterified at one or more of 2-, 3-, 5- or 6-hydroxyl group of L-ascorbic acid or stereoisomers thereof, for example, esters of phosphoric acid, sulfuric acid, straight or branched $C_2$–$C_{20}$ alkanoic acid or aryl carboxylic acid, and esters esterified by straight or branched $C_2$–$C_6$ alkoxycarbonyl and the like. Examples of the straight or branched $C_2$–$C_{20}$ alkanoic acid are acetic acid, propionic acid, butyric acid, isobutyric acid, valeric acid, isovaleric acid, hexanoic acid, octanoic acid, decanoic acid, lauric acid, myristic acid, palmitic acid, stearic acid and the like. Preferred example are the straight $C_{12}$–$C_{20}$ alkanoic acids. Examples of the aryl carboxylic acid include benzoic acid and the like. Examples of the straight or branched $C_2$–$C_6$ alkoxycarbonyl include methoxycarbonyl, ethoxycarbonyl, propoxycarbonyl, butoxycarbonyl, pentoxycarbonyl and the like. Preferred examples of the esters of phosphoric acid or sulfuric acid are ones esterified at the 2-hydroxyl group. Preferred examples of the esters of straight or branched $C_2$–$C_{20}$ alkanoic acid or aryl carboxylic acid, and the esters of straight or branched $C_2$–$C_6$ alkoxycarbonyl are those esterified at the 5- and/or 6-position(s).

"Stereoisomer of L-ascorbic acid" includes erythorbic acid and the like. "Glycoside of L-ascorbic acid" includes glycosides glycosidated at one or more of 2-, 3-, 5- and 6-hydroxyl groups of L-ascorbic acid or stereoisomers thereof, for example, 2-α-glycoside and the like (Biochem. Biophys. Acta, 1035, 44–50 (1990)). "Aminated derivatives of L-ascorbic acid" include derivatives substituted by amino at one or more of 2-, 3-, 5-and 6-hydroxyl groups of L-ascorbic acid or stereoisomers thereof, for example, scorbamic acid, erythroscorbamic acid and the like. "Ether of L-ascorbic acid" includes ethers formed at one or more of 2-, 3-, 5- or 6-hydroxyl group of L-ascorbic acid or stereoisomers thereof, for example, ethers of straight or branched $C_1$–$C_{20}$ alkyl at 5- or 6-hydroxyl groups.

Especially preferred examples of the L-ascorbic acid derivatives are L-ascorbic acid 2-phosphate, L-ascorbic acid 2-sulfate, L-ascorbic acid 6-palmitate, L-ascorbic acid 6-stearate, L-ascorbic acid 2-a-glycoside and the like.

"Salt of L-ascorbic acid or an L-ascorbic acid derivative" includes pharmaceutically acceptable salts of L-ascorbic acid and L-ascorbic acid derivatives. Examples of such salts are alkaline metal salts such as sodium salt, potassium salt and the like; alkaline earth metal salts such as magnesium salt, calcium salt, barium salt and the like; ammonium salts and the like.

L-Ascorbic acid, an L-ascorbic acid derivative or a salt thereof may be in the form of a solvate such as a hydrate and the like.

"Drug which causes lactic acid levels in blood to increase as a side effect" includes drugs which cause lactic acid levels in blood to increase as a side effect when administered, especially drugs which cause lactic acidosis by administration. Examples are amoxapine (psychotropic agent), theophylline (antitussive; expectorant), nalidixic acid (chemotherapeutic), calcium hopantenate (brain metabolic stimulant), azidothymidine, dideoxycytidine (HIV reverse transcriptase inhibitor), biguanides represented by formula 1:

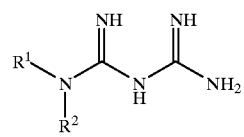

wherein $R^1$ and $R^2$ are as defined above, or a salt thereof, for example, metformin, phenformin, buformin ((1-butylbiguanide): medicament for diabetes) and the like, and the like. Those drugs and the salts thereof may be in the form of a solvate such as a hydrates and the like.

"Medical supplement which causes lactic acid levels in blood to increase as a side effect" includes medical supplements which are administered to maintain living bodies without pharmaceutical effects and which cause lactic acid levels in blood to increase as a side effect on administration, especially medical supplements which cause lactic acidosis on administration. Typical examples are high calorie transfusion, propylene glycol, ethylene glycol, pentoses such as xylitol, lactose, sorbitol and the like ("Igaku no ayumi", 183, 617(1997)) and the like.

"Lower alkyl" includes straight or branched $C_1$–C6 alkyl. Typical examples are methyl, ethyl, propyl, 2-propyl, butyl, 2-butyl, 3-methylpropyl, 1,1-dimethylethyl, pentyl, hexyl and the like.

"Aryl" includes $C_6$–$C_{10}$ aryl. Typical examples are phenyl, naphthyl and the like.

"Aralkyl" includes $C_7$–$C_{15}$ aralkyl. Typical examples are benzyl, phenylethyl, naphthylmethyl, naphthylpropyl and the like.

"Aryloxy-lower alkyl" includes lower alkyl substituted by aryloxy. Typical examples of the aryloxy are phenoxy, 1-naphthoxy, 2-naphthoxy and the like. Typical examples of the aryloxy-lower alkyl are 2-phenoxyethyl, 2-phenoxypropyl, 3-phenoxypropyl, 4-phenoxybutyl, 5-phenoxypentyl, 6-phenoxyhexyl, 2-(1-naphthoxy)ethyl, 2-(1-naphthoxy)propyl, 3-(1-naphthoxy)propyl, 4-(1-naphthoxy)butyl, 5-(1-naphthoxy)pentyl, 6-(1-naphthoxy)hexyl, 2-(2-naphthoxy)ethyl, 2-(2-naphthoxy)propyl, 3-(2-naphthoxy)propyl, 4-(2-naphthoxy)butyl, 5-(2-naphthoxy)pentyl, 6-(2-naphthoxy)hexyl and the like.

The substituent of "substituted aryl, substituted aralkyl and substituted aryloxy-lower alkyl" includes hydroxy, halogen atom, lower alkyl, lower alkoxy, amino, aminocarbonyl, aminosulfonyl, benzyloxy, phenyl, phenoxy, 2-phenylethyloxy, 3-phenylpropyloxy, cyano, nitro, acyl, acyloxy and the like. The position(s) of the substituent(s) on aralkyl and aryloxy-lower alkyl are preferably any position (s) on the aryl moiety. The number of the substituent(s) is 1 to 5, preferably 1 to 3.

Typical examples of the substituted aryl are 2-nitrophenyl, 4-methoxyphenyl, 2,3-dimethoxyphenyl, 2,3, 4-trimethoxyphenyl, 4-methoxycarbonylphenyl, 4-cyanophenyl, 4-methylphenyl, 3,4-difluorophenyl, 4-bromophenyl, 4-(N,N-dimethylaminocarbonyl)phenyl, 4-(N,N-dimethylaminosulfonyl)phenyl, 4-benzyloxyphenyl, 4-hydroxyphenyl, 4-biphenyl, N,N-dimethylaminophenyl, 3-phenoxyphenyl, 3-(2-phenylethyloxy)phenyl, 3-(3-phenylpropyloxy)phenyl and the like.

Typical examples of the substituted aralkyl are 2-nitrobenzyl, 4-methoxybenzyl, 2,3-dimethoxybenzyl, 2,3, 4-trimethoxybenzyl, 4-methoxycarbonylbenzyl, 4-cyanobenzyl, 4-methylbenzyl, 3,4-difluorobenzyl, 4-bromobenzyl, 4-(N,N-dimethylaminocarbonyl)benzyl, 4-(N,N-dimethylaminosulfonyl)benzyl, 4-benzyloxybenzyl, 4-hydroxybenzyl, 4-phenylbenzyl, N,N-dimethylaminobenzyl, 3-phenoxybenzyl, 3-(2-phenylethyloxy)benzyl, 3-(3-phenylpropyloxy)benzyl, 2-(2-nitrophenyl)ethyl, 2-(4-methoxyphenyl)ethyl, 2-(2,3-dimethoxyphenyl)ethyl, 2-(2,3,4-trimethoxyphenyl)ethyl, 2-(4-methoxycarbonylphenyl)ethyl, 2-(4-cyanophenyl) ethyl, 2-(4-methylphenyl)ethyl, 2-(3,4-difluorophenyl)ethyl, 2-(4-bromophenyl)ethyl, 2-(4-(N, N-dimethylaminocarbonyl)phenyl)ethyl, 2-(4-(N,N-dimethylaminosulfonyl)phenyl)ethyl, 2-(4-phenylethyloxyphenyl)ethyl, 2-(4-hydroxyphenyl)ethyl, 2-(4-phenylphenyl)ethyl, 2-(N,N-dimethylaminophenyl) ethyl, 2-(3-phenoxyphenyl)ethyl, 2-(3-(2-phenylethyloxy) phenyl)ethyl, 2-(3-(3-phenylpropyloxy)phenyl)ethyl and the like.

Typical examples of the substituted aryloxy-lower alkyl are 2-(2-nitrophenyl)oxyethyl, 2-(4-methoxyphenyl) oxyethyl, 3-(4-methoxyphenyl)oxypropyl, 2-(2,3-dimethoxyphenyl)oxypropyl, 3-(2,3,4-trimethoxyphenyl) oxypropyl, 2-(4-methoxycarbonylphenyl)oxyethyl, 2-(4-cyanophenyl)oxyethyl, 4-(4-methylphenyl)oxybutyl, 2-(3,4-difluorophenyl)oxyethyl, 2-(4-bromophenyl)oxyethyl, 5-(4-(N,N-dimethylaminocarbonyl)phenyloxypentyl, 2-(4-(N,N-dimethylaminosulfonyl)phenyl)oxyethyl, 2-(4-benzyloxyphenyl)oxyethyl, 2-(4-hydroxyphenyl)oxyethyl, 2-(4-phenylphenyl) oxyethyl, 2-(N,N-dimethylaminophenyl)oxyethyl, 2-(3-phenoxyphenyl) oxyethyl, 2-(3-(2-phenylethyloxy)phenyl)oxyethyl, 2-(3-(3-phenylpropyloxy)phenyl)oxyethyl and the like.

L-Ascorbic acid, L-ascorbic acid derivatives and the salts thereof have inhibitory effect against gluconeogenesis as shown in Experiment 5, and they can enhance the inhibitory effect against gluconeogenesis of biguanides represented by formula 1 which are useful as a medicament for diabetes. Therefore, "the pharmaceutical composition containing L-ascorbic acid, an L-ascorbic acid derivative or a salt thereof and a biguanide represented by formula 1 or the salt thereof" and "the salt formed from L-ascorbic acid or an L-ascorbic acid derivative and a biguanide represented by formula 1" are useful as medicaments for treating diabetes.

"Saturated heterocyclic ring which $R^1$ and $R^2$ are taken together with the nitrogen atom to form" includes 3- to 7-membered, nitrogen-containing saturated heterocyclic rings containing at least one nitrogen, sulfur or oxygen atom. Typical examples include 3-membered nitrogen-containing saturated heterocyclic rings such as aziridine and the like; 4-membered nitrogen-containing saturated heterocyclic rings such as azetidine and the like; 5-membered nitrogen-containing saturated heterocyclic rings such as imidazolidine, pyrrolidine, pyrazoline, thiazolidine, oxazolidine and the like; 6-membered nitrogen-containing saturated heterocyclic rings such as piperidine, piperazine, morpholine and the like; 7-membered nitrogen-containing saturated heterocyclic rings such as homopiperidine and the like; and the like.

The salts of "amoxapine, theophylline, metformin, phenformin, buformin, nalidixic acid, hopantenic acid, azidothymidine, dideoxycytidine or a biguanide represented by formula 1" include pharmaceutically acceptable salts thereof. Typical examples include salts with inorganic acids such as the hydrochloride, sulfate, hydrobromide, phosphate salts and the like; salts with organic acids such as the oxalate, malonate, fumarate, benzenesulfonate, methanesulfonate salts and the like; salts with inorganic bases such as the sodium, potassium, calcium, barium, ammonium salts and the like; salts with organic bases such as the lysine, triethylammonium salts and the like. The salt may be in the form of a solvate such as a hydrate and the like.

The basic group in "drug having basic group(s) which causes lactic acid levels in blood to increase as a side effect" includes basic groups which are able to form salts with L-ascorbic acid or L-ascorbic acid derivatives. Typical examples include optionally substituted amino, optionally substituted cyclic amino, hydroxyamino, optionally substituted guanidino, optionally substituted amidino and the like.

"Cyclic amino" includes 3- to 7-membered cyclic amino containing at least one of nitrogen, sulfur and oxygen atoms. Typical examples include 3-membered cyclic amino such as aziridinyl and the like; 4-membered cyclic amino such as azetidinyl and the like; 5-membered cyclic amino such as imidazolidinyl, pyrrolidinyl, pyrazolinyl, thiazolidinyl, oxazolidinyl and the like; 6-membered cyclic amino such as piperidinyl, piperazinyl, morpholinyl and the like; 7-membered cyclic amino such as homopiperidinyl and the like; and the like.

The substituent of "substituted amino, substituted cyclic amino, substituted guanidino and substituted amidino" includes lower alkyl, optionally substituted aralkyl, optionally substituted aryl, optionally substituted aryloxy-lower alkyl and the like. They may be substituted by two substituents.

Typical examples of substituted amino include methylamino, dimethylamino, ethylamino, diethylamino, butylamino, benzylamino, 4-aminobenzylamino, 3-methoxybenzylamino, 2-phenylethylamino and the like.

Typical examples of substituted guanidino include methylguanidino, dimethylguanidino, ethylguanidino, diethylguanidino, butylguanidino, benzylguanidino, 4-aminobenzylguanidino, 3-methoxybenzylguanidino, 2-phenylethylguanidino and the like.

Typical examples of the substituted amidino are methylamidino, dimethylamidino, ethylamidino, diethylamidino, butylamidino, benzylamidino, 4-aminobenzylamidino, 3-methoxybenzylamidino, 2-phenylethylamidino and the like.

Preferred examples of the "salt formed from L-ascorbic acid or an L-ascorbic acid derivative and a drug having basic group(s) which causes lactic acid levels in blood to increase as a side effect" include "salts formed from L-ascorbic acid or an L-ascorbic acid derivative and a biguanide represented by formula 1", and more preferred are "salts formed from L-ascorbic acid or an L-ascorbic acid derivative and metformin, buformin or phenformin". Typical examples include metformin L-ascorbate, metformin L-ascorbic acid 2-phosphate, metformin L-ascorbic acid 2-sulfate, metformin L-ascorbic acid 6-palmitate, metformin L-ascorbic acid 6-stearate, buformin L-ascorbate, buformin L-ascorbic acid 2-phosphate, buformin L-ascorbic acid 2-sulfate, buformin L-ascorbic acid 6-palmitate, buformin L-ascorbic acid 6-stearate, phenformin L-ascorbate, phenformin L-ascorbic acid 2-phosphate, phenformin L-ascorbic acid 2-sulfate, phenformin L-ascorbic acid 6-palmitate, phenformin L-ascorbic acid 6-stearate and the like.

The biguanide represented by formula 1 can be produced for example by the following method:

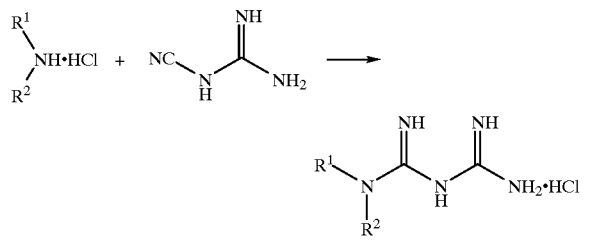

wherein $R^1$ and $R^2$ are as defined above.

The hydrochlorides of the biguanides represented by formula 1 can be produced, for example, by heating a mixture of a compound represented by the formula: $R^1R^2NH$ HCl and dicyandiamide at 120° C. or above without or in a solvent. Preferred reaction solvents are high-boiling point ethers such as methyl cellosolve and the like. The hydrochloride of biguanide of formula 1 can be changed to free base or another salt by a conventional method. The free base of biguanide of formula 1 can be produced for example by letting the hydrochloride flow through ion exchange resin column according to the method described in JP 50-53520 (A). The free base can be also produced by neutralizing the hydrochloride by sodium hydroxide solution or the like and concentrating the mixture in vacuo, followed by extraction from the residue with an organic solvent such as acetone.

"Salt formed from L-ascorbic acid or an L-ascorbic acid derivative and a drug having basic group(s) which causes lactic acid levels in blood to increase as a side effect" can be produced by a conventional method. The salt can be formed for example by mixing L-ascorbic acid or an L-ascorbic acid derivative and "a drug having basic group(s) which causes lactic acid levels in blood to increase as a side effect" in an inactive solvent. The inactive solvents include alcohols such as methanol, ethanol, 2-propanol and the like, water, acetone, mixtures of any of these and the like. The amount of L-ascorbic acid or an L-ascorbic acid derivative is selected for example from about 0.3 to about 3 equivalent, preferably about 1 to about 1.5 equivalent, per 1 equivalent of the "drug having basic group(s) which causes lactic acid levels in blood to increase as a side effect."

When such a salt can be easily crystallized, the salt may be produced in a crystalline form, and may be purified by recrystallization if needed. Solvents for recrystallization include alcohols such as methanol, ethanol, 2-propanol and the like, ethers such as diethyl ether and the like, esters such as ethyl acetate and the like, aromatic hydrocarbons such as toluene and the like, ketones such as acetone and the like, hydrocarbons such as hexane and the like, water and mixture of any of these and the like.

The salt formed from L-ascorbic acid or an L-ascorbic acid derivative and a biguanide of formula 1 can be produced in a crystalline form for example by mixing L-ascorbic acid or the L-ascorbic acid derivative and the free biguanide in an inert solvent. The amount of L-ascorbic acid or the L-ascorbic acid derivative is preferably about 1 to about 1.5 equivalent per 1 equivalent of the biguanide of formula 1. Inert solvents include alcohols such as methanol, ethanol, 2-propanol and the like, water, acetone and mixture of any of these. The crystallization temperature is for example about −20 to about 70° C., preferably about −10 to about 20° C.

An "L-ascorbic acid, an L-ascorbic acid derivative or a salt thereof" as a medicament for reducing lactic acid levels in blood, "a pharmaceutical composition containing L-ascorbic acid, an L-ascorbic acid derivative or a salt thereof, and a drug or a medical supplement which causes lactic acid levels in blood to increase as a side effect" and "a salt formed from L-ascorbic acid or an L-ascorbic acid derivative and a drug having basic group(s) which causes lactic acid levels in blood to increase as a side effect" may be administered orally or parenterally. Pharmaceutical forms for oral administration include generally acceptable forms, for example, tablets, capsules, granules, fine granules, powders, pills, syrups, suspensions and the like. Pharmaceutical forms for parenteral administration include for example injections such as solutions, emulsions, suspensions and the like; suppository for administration through the rectum; dermal preparations and the like. These compositions can be prepared by mixing the active compound with conventional carriers, excipients, binders, stabilizers and the like. Injections may contain buffers, solubilizers, agents for influencing osmotic pressure and the like.

The dose for administration of "L-Ascorbic acid, an L-ascorbic acid derivative or a salt thereof" as a medicament for reducing lactic acid levels in blood generally varies depending on the severity of the symptoms, the patient's age, body weight, administration route and the like. L-Ascorbic acid, L-ascorbic acid derivatives and salts thereof are usually administered to an adult (body weight: 60 kg) in a dose of about 50 mg to about 10 g, preferably about 100 mg to about 5 g, more preferably about 300 mg to about 3 g per day in one portion or several portions.

The dose for administration of "pharmaceutical composition containing L-ascorbic acid, an L-ascorbic acid derivative or a salt thereof, and a drug or a medical supplement which causes lactic acid levels in blood to increase as a side effect" generally varies depending on the severity of the symptoms, the patient's age, body weight, administration route and the like. L-Ascorbic acid, an L-ascorbic acid derivative or a salt thereof in the pharmaceutical composition is usually administered to an adult (body weight: 60 kg) in a dose of about 50 mg to about 10 g, preferably about 100 mg to about 5 g, more preferably about 300 mg to about 3 g per day in one portion or several portions. A drug or a medical supplement which causes lactic acid levels in blood to increase as a side effect in the pharmaceutical composition may be administered in the usual dose in which the drug or the medical supplement has their own effects. When the drug is a biguanide represented by formula 1 or the salt thereof, the drug is usually administered to an adult (body weight: 60 kg) in a dose of about 100 mg to about 5 g, preferably about 300 mg to about 3 g, more preferably about 500 mg to about 2 g per day in one portion or several portions.

The dose for administration of "salt formed from L-ascorbic acid or an L-ascorbic acid derivative and a drug having basic group(s) which causes lactic acid levels in blood to increase as a side effect" generally varies depending on the severity of the symptoms, the patient's age, body weight, administration route and the like. The salt may be administered in the usual dose in which "the drug having basic group(s) which causes lactic acid levels in blood to increase as a side effect" contained in the salt has its own effects. However, when the amount of "L-ascorbic acid or an L-ascorbic acid derivative" contained in the salt is lower than the necessary dose for reducing lactic acid levels in blood, additional "L-ascorbic acid, an L-ascorbic acid derivative or a salt thereof" may be administered together. When the salt is "salt formed from L-ascorbic acid or an L-ascorbic acid derivative and a biguanide represented by formula 1", the salt is usually administered to an adult (body weight: 60 kg) in a dose of about 100 mg to about 20 g, preferably about 200 mg to about 10 g, more preferably about 600 mg to about 6 g per day in one portion or several portions.

EXAMPLES

Example 1

Production of Metformin L-ascorbate

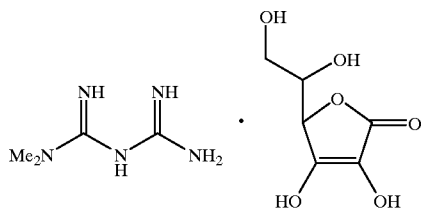

Metformin hydrochloride (49.68 g: 0.3 mol) was dissolved in pure water, and neutralized with 2N sodium hydroxide aqueous solution (150 mL). The mixture was condensed in vacuo until it contained about 30 mL of water. To the mixture was added 2-propanol (300 mL) and stirred at room temperature for 30 minutes. The mixture was filtered and the residue was washed with acetone. The filtrate and the acetone were gathered and the solvent was evaporated in vacuo. Acetone (500 mL) and magnesium sulfate were added to the residue, stirred and filtered. The filtrate was concentrated in vacuo to give free metformin (32.9 g: yield 85%) as white prisms.

The solution of free metformin (32.9 g: 255 mmol) obtained above in methanol (150 mL) was added dropwise to the solution of L-ascorbic acid (44.9 g: 255 mmol) in methanol (600 mL) with stirring in ice-water bath for 30 minutes. The obtained slurry was stirred in ice-water bath for 30 minutes, at room temperature for 30 minutes, and then in ice-water bath for 1 hour. The crystals were collected by filtration, washed with methanol (100 mL) and acetone (500 mL×2) successively, and dried in vacuo to give metformin L-ascorbate (56.9 g: yield from free metformin 73%) as white powders. The filtrate were combined and concentrated to 200 mL. The formed crystals was collected by filtration, and washed by methanol (20 mL) and acetone (100 mL), followed by drying in vacuo to give metformin L-ascorbate (7.2 g: yield 9%).

White needles (methanol): mp 143–5° C. (decomp.); Elemental Analysis ($C_{10}H_{19}N_5O_6$); Calculated (%): C 39.34, H 6.27, N 22.94; Found (%): C 39.24, H 6.27, N 22.82; IRγ (KBr, $cm^{-1}$) 3337, 3209, 2935, 1702, 1660, 1644, 1585, 1542, 1420, 1406, 1137, 1108, 1053; $^1$H-NMR δ (DMSO-$D_6$, ppm) 2.92(6H,s), 3.30(2H,m), 3.46(1H,dd,J= 11.2 and 8.3Hz), 3.85(1H,d,J=7.6Hz), 4.75(1H,br), 6.58(4H, br), 7.20(2H,br).

Example 2

Production of Metformin L-ascorbic Acid 2-phosphate 1.5 Hydrates

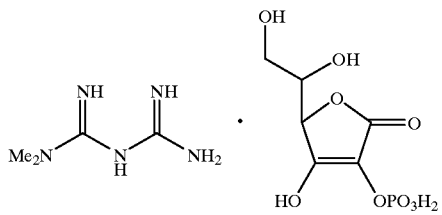

L-Ascorbic acid 2-phosphate 2/3 magnesium salts n hydrates (Wako Pure Chemicals: 23.5 g) was dissolved in water (200 mL), and was let flow through column chromatography with ion exchange resin (A.G.IR-120B(H): Organo Ltd.: 400 mL), and was eluted with water. The first 500 mL of eluent which was acidic was collected. To the collected eluent was added free metformin (7.7 g: 52 mmol), and concentrated to about 100 mL. To the mixture was added acetone (800 mL) at room temperature with stirring to form white crystals gradually. The mixture was stirred for another 1 hour. The crystals were collected by filtration and washed with acetone/water (10:1) and acetone, followed by drying in vacuo to give metformin L-ascorbic acid 2-phosphate 1.5 hydrates (19.34 g).

White prisms (washed with acetone/water): mp 105–7° C. Elemental Analysis ($C_{10}H_{20}N_5O_9P$ 1.5 $H_2O$); Calculated (%): C 29.13, H 5.62, N 16.99, P 7.51; Found (%): C 28.98, H 5.83, N 16.96, P 8.10; IR γ (KBr, $cm^{-1}$) 3288, 2950, 1736, 1693, 1662, 1593, 1507, 1480, 1134, 1104, 1080, 1037; $^1$H-NMR δ ($D_2O$, ppm) 3.10(6H,s), 3.77(2H,d,J=6.3 Hz), 3.46(1H,td,J=6.3 and 2.0 Hz), 4.95(1H,d,J=2.0 Hz).

Materials and Methods

Materials

Distilled water for injection (Otsuka pharmaceuticals), saline (Otsuka pharmaceuticals) and metformin hydrochloride (Sigma) were purchased and used. All other reagents and chemicals used were at commercial analytical grade.
Method to Prepare Metformin Solution and Other Acid Solutions Metformin hydrochloride was dissolved in distilled water for injection to give 100 mM solution. L-Ascorbic acid, citric acid, succinic acid and malic acid were dissolved in distilled water for injection to give 400 mM solution.

Cell Culture

3T3-L1 cells (ACTT CL173: preadipose cells from fetal mouse) were grown on gelatin coated 96-well plate ($2 \times 10^3$ cells/well) in DMEM (Dulbecco's modified Eagle medium) supplemented with 10% calf serum under the 5% $CO_2$/95% air condition until getting sufficiently confluent. Then the cells were differentiated to adipocytes according to the following procedure. At first the medium was changed to DMEM containing 0.5 mM 1-methy-3-isobutylxanthine, 1 μM dexamethasone, 10 μg/mL insulin, 8 μg/mL biotin and 10% fetal calf serum, and after 48 hr the medium was changed to DMEM containing 1 μg/mL insulin, 8 μg/mL biotin and 10% fetal calf serum. After maintenance for 48 hr, the medium was changed to DMEM containing 8 μ/mL biotin and 10% fetal calf serum. The medium was changed with the same fresh medium every 48 hr until experiments.

Hepatocytes primary culture was prepared by Seglen's method (Methods Cell Biol., 13, 29–83 (1976)). Hepatocytes were isolated from a male Wistar rat. The isolated hepatocytes were grown on gelatin coated 24-well plate ($3\times10^5$ cells/well) in Williams E medium containing 10 nM dexamethasone and 5% fetal calf serum under the 37° C., 5% $CO_2$/95% air condition for 24 hr.

Animals

Breeding Condition

Animals that did not have any indisposition during 1-week quarantine after purchase were used for experiments. The animals were maintained in a room which was managed in the condition: 23±2° C., 55±10% humidity, air exchange: more than 10 times/hr, light time: 8:00 a.m. to 8:00 p.m. Less than 5 heads of the animals were housed in each plastic cage (31×36×17.5 cm) with shavers on floors during quarantine and breeding. To the animals were fed solid feed CE-2 (Nihon CREA) and filtrated water from bottles or automatic system ad libitum. The animals were weighed by automatic animal scale (Shimadzu).

5/6 Nephrectomy Rats

5/6 Nephrectomy (2/3 of left kidney and all right kidney) rats were prepared by Hamburger's method (Pathological Biology, 18, 403–406 (1970)). After 5-week old Wistar rats were acclimatized for 7 to 10 days, 2/3 of left kidney were removed. After the rats were bred and observed for 7 days, all right kidney was removed. After the rats were bred and observed for 7 to 10 days, the rats were used for experiments.

KKAy Mice

10-Week old KKAy mice (individually housed during their 6- to 10-week), a model for insulin-resistant diabetes, were obtained from Nihon CREA. To determine diabetic stage in KKAy mice, urine glucose levels of the mice were checked with urine glucose level test paper (Wako, Pretest 2 g). It was affirmed that the urine glucose levels of all mice used in the experiment were more than 1000 mg/dL. After 7-day acclimatization, the mice were used for the experiment.

Method to Measure Lactic Acid Levels

Lactic acid levels were measured by enzyme assay on lactate dehydrogenase and glutamate pyruvate transaminase, using Lactate Test BMY (Boehringer Mannheim).

Method to Measure Glucose Levels

Glucose levels were measured by mutarotase/glucose oxidase method, using Glucose Test CII (WAKO).

Method to Measure Blood Biochemicals Levels

Blood biochemicals levels were determined by using Cynchron CX3 delta (Beckman). Blood creatinine levels were measured by alkaline picric acid method. Blood urea nitrogen levels were measured by urease enzyme methods.

Statistical Analysis

Statistical significance of biochemicals levels etc. was evaluated using Dunnett's test or Tukey's test.

Example 1

The Effects of L-ascorbic Acid Against Lactic Acid Increase Induced by Metformin Hydrochloride in 3T3-L1 Adipocytes To the plate of the differentiated 3T3-L1 cells were added metoformin hydrochloride (10 mM) and various acids (40 mM), and the differentiated 3T3-L1 cells were incubated under 30% $O_2$/5% $CO_2$ condition for 24 hr. Lactic acid levels in the medium were measured. Consequently as shown in Table 1, L-ascorbic acid prevented lactic acid increase induced by metformin hydrochloride.

TABLE 1

| Concentration of Metformin hydrochloride (mM) | Additive (40 mM) | Lactic acid levels (mg/dL) |
|---|---|---|
| 0 | — | 53 |
| 10 | — | 154 |
| | L-Ascorbic acid | 73 |
| | Citric acid | 155 |
| | Succinic acid | 145 |
| | Malic acid | 143 |

Three independently executed experiments indicated almost the same results.

Example 2

The Effect of L-ascorbic Acid Against Lactic Acidosis Induced by Metformin Hydrochloride in 5/6 Nephrectomy Rats The effects of metformin hydrochloride, metformin L-ascorbate and metformin hydrochloride+L-ascorbic acid against lactic acidosis were examined using 5/6 nephrectomy rats. The experimental schedule was as follows. 5/6 Nephrectomy rats were divided into four groups according to their weight, blood urea nitrogen levels and serum creatinine levels after preliminary breeding and observation after purchase. The rats of the groups were treated with vehicle (saline), metformin hydrochloride, metformin L-ascorbate and metformin hydrochloride+L-ascorbic acid p.o. twice a day for 4 days. The volume of administrated liquids was 5 mL/kg/dose. Metformin hydrochloride 250 mg/kg/dose (500 mg/kg/day), metformin L-ascorbate 461 mg/kg/dose (922 mg/kg/day), metformin hydrochloride 250 mg/kg/dose (500 mg/kg/day)+L-ascorbic acid 266 mg/kg/dose (532 mg/kg/day) were dissolved in vehicle (saline) that was used in negative control group, and administered, so that the compounds of each group contained the same moles of metformin. The number of the animals used was 5 heads for vehicle group, 5 heads for metformin hydrochloride group, 5 heads for metformin L-ascorbate group and 3 heads for metformin hydrochloride+L-ascorbic acid group. Blood was collected from tail vein under ether anesthetics at the day 5, and the blood lactic acid levels were measured. Blood lactic acid levels are indicated in table 2.

TABLE 2

| | Blood lactic acid levels (mg/dL) |
|---|---|
| Saline | 26.9 ± 2.9 |
| Metformin hydrochloride | 52.5 ± 9.6 (**) |
| Metformin L-ascorbate | 40.2 ± 6.2 (†)(*) |
| Metformin hydrochloride + L-ascorbic acid | 41.0 ± 11.6 |

Blood lactic acid levels in metformin hydrochloride group were significantly higher than vehicle group (**:$P<0.01$). Blood lactic acid levels in metformin L-ascorbate group were significantly higher than vehicle group (*:$P<0.05$), and significantly lower than metformin hydrochloride group (†:$P<0.05$). Almost the same result was observed in metformin L-ascorbate group as one in metformin hydrochloride+L-ascorbic acid group.

Example 3

Examination of the Influence of L-ascorbic Acid to the Metformin's Effect for Reducing Blood Sugar Levels in Diabetic Model Animals (KKAy mice)

The effect for reducing blood sugar levels which is the main effect of metformin was analyzed using metformin hydrochloride, L-ascorbic acid and metformin L-ascorbate in diabetic model animals (KKAy mice). The experimental schedule was as follows. The mice were divided into four groups according to their weight after preliminary breeding after purchase. The mice of each groups were treated with saline, metformin hydrochloride, 1-ascorbic acid and metformin L-ascorbate p.o. twice a day for 5 days. The volume of administrated liquids was 10 mL/kg/dose. Metformin hydrochloride 600 mg/kg/dose (1200 mg/kg/day), L-ascorbic acid 800 mg/kg/dose (1600 mg/kg/day) and metformin L-ascorbate 1400 mg/kg/dose (2800 mg/kg/day) were administered. Blood was collected from main vein under ether anesthetization, after 2hr from the last administration. Blood glucose levels in each group are indicated in table 3.

TABLE 3

|  | Blood glucose levels (mg/dL) |
| --- | --- |
| Saline | 480.0 ± 114.5 |
| Metformin hydrochloride | 247.6 ± 30.2 (**) |
| L-ascorbic acid | 392.8 ± 45.3 |
| Metformin L-ascorbate | 270.3 ± 78.2 (**) |

Significant effects for reducing blood glucose levels were observed in metformin hydrochloride group and metformin L-ascorbate group.

Example 4

Examination of the Influence of L-ascorbic Acid to the Metformin's Effect for Reducing Blood Sugar Levels in Diabetic Model Animals (KKAy mice)

The effect for reducing blood sugar levels which is the main effect of metformin was analyzed using metformin hydrochloride, L-ascorbic acid and metformin hydrochloride+L-ascorbic acid in diabetic model animals (KKAy mice). The experimental schedule was as follows. The mice were divided into four groups according to their weight after preliminary breeding after purchase. The mice of each groups were treated with saline, metformin hydrochloride, 1-ascorbic acid and metformin L-ascorbate p.o. twice a day for 5 days. The volume of administrated liquids was 10 mL/kg/dose. Metformin hydrochloride 600 mg/kg/dose (1200 mg/kg/day), L-ascorbic acid 2900 mg/kg/dose (5800 mg/kg/day) and metformin hydrochloride 600 mg/kg/dose (1200 mg/kg/day)+L-ascorbic acid 2900 mg/kg/dose (5800 mg/kg/day) were administered. Blood was collected from main vein under ether anesthetization, after 2 hr from the last administration. Blood glucose levels in each group are indicated in table 4.

TABLE 4

|  | Blood glucose levels (mg/dL) |
| --- | --- |
| Saline | 454.2 ± 93.6 |
| Metformin hydrochloride | 286.5 ± 63.1 (**) |
| L-ascorbic acid | 367.0 ± 45.3 |
| Metformin hydrochloride + L-ascorbic acid | 269.2 ± 67.4 (**) |

Significant effects for reducing blood glucose levels were observed in metformin hydrochloride group and metformin hydrochloride+L-ascorbic acid group.

Example 5

Examination of the Effect of L-ascorbic Acid to the Inhibitory Effect Against Gluconeogenesis of Metformin Hydrochloride in Rat Hepatocytes Primary Culture After the plates of hepatocytes primary culture were washed by phosphate buffer twice, the medium were changed to Hanks solution containing 0.1% fructose (depletion glucose). Each well was treated with metformin hydrochloride (1 or 3 mM), L-ascorbic acid (1 or 3 mM) or metformin hydrochloride+L-ascorbic acid (each 1 or 3 mM) and then incubated for 6 hr at 37° C. under 5% $CO_2$/95% air. Glucose levels (mg/dL) in the medium were measured. The results are indicated in table 5.

TABLE 5

|  | None | 1 mM | 3 mM |
| --- | --- | --- | --- |
| Metformin hydrochloride | 18.7 | 17.7 | 15.2 |
| L-ascorbic acid | — | 14.6 | 10.6 |
| Metformin hydrochloride + L-ascorbic acid | — | 13.5 | 9.0 |

Gluconeogenesis was reduced by addition of metformin hydrochloride or L-ascorbic acid. Inhibitory effect against gluconeogenesis was enhanced by coexistence of metformin hydrochloride and L-ascorbic acid.

Preparation 1

Preparation of Tablets

A 200 mg tablet is prepared by mixing the following ingredients followed by compressing the mixture into a tablet.

| Metformin | 50 mg |
| --- | --- |
| L-ascorbic acid | 50 mg |
| Lactic acid | 70 mg |
| Corn starch | 15 mg |
| Low substituted Hydroxypropylcellulose | 8 mg |
| Polyvinylpyrrolidone | 6 mg |
| Magnesium stearate | 1 mg |
| Total | 200 mg |

Preparation 2

Preparation of Tablets

A 200 mg tablet is prepared by mixing the following ingredients followed by compressing the mixture into a tablet.

| Metformin | 50 mg |
| --- | --- |
| L-ascorbic acid | 50 mg |
| D-mannitol | 60 mg |
| Crystalline cellulose | 25 mg |
| Carmellose Calcium | 8 mg |
| Hydroxypropylmethylcellulose | 6 mg |
| Magnesium stearate | 1 mg |
| Total | 200 mg |

Preparation 3

Preparation of Capsules

A capsule is prepared by mixing the following ingredients followed by filling the mixture into a capsule.

| | |
|---|---|
| Metformin | 50 mg |
| L-ascorbic acid | 50 mg |
| D-mannitol | 110 mg |
| Low substituted Hydroxypropylcellulose | 8 mg |
| Magnesium stearate | 2 mg |
| Total | 220 mg |

Preparation 4

Preparation of Capsules

A capsule is prepared by mixing the following ingredients followed by filling the mixture into a capsule.

| | |
|---|---|
| Metformin | 50 mg |
| L-ascorbic acid | 50 mg |
| D-mannitol | 43.5 mg |
| Carmellose Calcium | 5 mg |
| Magnesium stearate | 1.5 mg |
| Total | 150 mg |

Preparation 5

Preparation of Powders

Powders are prepared by mixing the following ingredients followed by granulating the mixture optionally.

| | |
|---|---|
| Metformin | 250 mg |
| L-ascorbic acid | 250 mg |
| Lactic acid | 400 mg |
| Corn starch | 90 mg |
| Magnesium stearate | 10 mg |
| Total | 1000 mg |

In the above preparations, preparations containing metformin and L-ascorbic acid are shown. Other "pharmaceutical composition containing L-ascorbic acid, an L-ascorbic acid derivative or a salt thereof, and a drug or a medical supplement which causes lactic acid levels in blood to increase as a side effect", "medicament for reducing lactic acid levels in blood containing L-ascorbic acid, an L-ascorbic acid derivative or a salt thereof as an active ingredient" and preparation containing "salt formed from L-ascorbic acid or an L-ascorbic acid derivative and a drug having basic group(s) which causes lactic acid levels in blood to increase as a side effect" can be produced by the same method.

Industrial Applicability

The present invention can provide a medicament for reducing lactic acid levels in blood. The present invention can also provide a pharmaceutical composition or a compound with a reduced side effect, which contains a drug or a medical supplement which causes lactic acid levels in blood to increase as a side effect.

What is claimed is:

1. A method for reducing lactic acidosis caused by a drug which has lactic acidosis as a side effect, which comprises administering L-ascorbic acid, an L-ascorbic acid derivative or a salt thereof to a subject in need thereof.

2. A method according to claim 1 wherein the drug is amoxapine, theophylline, metformin, phenformin, buformin, nalidixic acid, hopantenic acid, azidothymidine, dideoxycytidine, or a salt thereof.

3. A method according to claim 1 wherein the drug is a biguanide represented by formula 1:

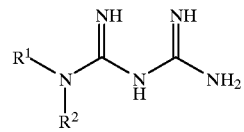

wherein
   $R^1$ is hydrogen or lower alkyl;
   $R^2$ is lower alkyl, optionally substituted aryl, optionally substituted aralkyl or optionally substituted aryloxy-lower alkyl; or $R^1$ and $R^2$ are taken together with the nitrogen atom to form a saturated heterocyclic ring, or a salt thereof.

4. A method according to claim 1, claim 2 or claim 3 wherein L-ascorbic acid, the L-ascorbic acid derivative or the salt thereof is L-ascorbic acid.

5. A method according to claim 4 wherein the drug is metformin, phenformin or buformin.

6. A method according to claim 5 wherein the drug is metformin.

\* \* \* \* \*